(12) United States Patent
Wang et al.

(10) Patent No.: US 8,062,678 B2
(45) Date of Patent: Nov. 22, 2011

(54) **EXTRACTIVE OF *PIPER LAETISPICUM* C.DC., ITS PROCESS AND ITS USES**

(76) Inventors: Ezhou Wang, Shanghai (CN); Yi Jiang, Shanghai (CN)

( * ) Notice: Subject to any disclaimer, the term of this patent is extended or adjusted under 35 U.S.C. 154(b) by 539 days.

(21) Appl. No.: 11/720,616

(22) PCT Filed: Nov. 28, 2005

(86) PCT No.: PCT/CN2005/002034
§ 371 (c)(1),
(2), (4) Date: Jul. 29, 2009

(87) PCT Pub. No.: WO2006/058487
PCT Pub. Date: Jun. 8, 2006

(65) Prior Publication Data
US 2009/0297642 A1    Dec. 3, 2009

(30) Foreign Application Priority Data
Dec. 1, 2004   (CN) .......................... 2004 1 0084791

(51) Int. Cl.
*A01N 65/00* (2009.01)

(52) U.S. Cl. .................................................... 424/725
(58) Field of Classification Search .................. None
See application file for complete search history.

(56) References Cited

U.S. PATENT DOCUMENTS
6,858,648 B2 *  2/2005  Pan et al. ..................... 514/464

FOREIGN PATENT DOCUMENTS
CN    1291481    4/2001
CN    1532182    9/2004

* cited by examiner

*Primary Examiner* — Michael Meller
(74) *Attorney, Agent, or Firm* — Sutherland Asbill & Brennan LLP

(57) ABSTRACT

This is about a type of *Piper laetispicum* C.DC. extract and the preparation method thereof as well as the application of the extract in preparing drugs, healthcare products and food additives for treating and/or preventing diseases related to monoamine transmitters such as 5-hydroxytryptamine, noradrenaline and dopamine. The extract is obtained through impregnating or percolating at normal temperature or $\leq 70°$ C., or is obtained through supercritical fluid extraction method, and in comparison with the existing reflux method, it has higher alkaloid content and higher biological activity.

4 Claims, No Drawings

EXTRACTIVE OF *PIPER LAETISPICUM* C.DC., ITS PROCESS AND ITS USES

CROSS REFERENCE TO RELATED APPLICATIONS

This application claims the priority benefit of PCT/CN2005/002034 filed on Nov. 28, 2005 and Chinese Application 200410084791.7 filed on Dec. 1, 2004.

BACKGROUND

1. Field of Technology

This invention involves the medical plant *Piper laetispicum* C.DC., and is specifically about the method for preparing *Piper laetispicum* C.DC. extract, the extract prepared and obtained by making use of the method, and the application of the extract.

2. Background Technology

Diseases related to the metabolism of monoamine transmitters such as 5-hydroxytryptamine (5-HT), noradrenaline (NA) and dopamine (DA) are currently one of the primary kinds of diseases that affect human health, and as indicated by WHO data, the total burden of such diseases thus incurred is second only to coronary artery disease in developed countries, while neuropsychopathy is ranked as first among the total burdens of diseases in China, which is approximately ⅕ of the total burdens of diseases. For example, many communities and medical researches have revealed that depression and anxiety disorders both have relatively high incidence rates, and a survey of syndromes throughout the entire United States indicates that 17.3% of ordinary people have encountered depression onset and 24.5% of people have experienced anxiety disorders at a certain period of time in their lives, and all these researches consistently indicate in most cases that many people will face the problems of depressive disorders or anxiety disorders in the future. For some special groups of people, such as disabled people, chronic physical disease patients, drug abusers, those who depend on alcohol and celibatarians, their incidence rate and morbidity rate are even higher for diseases related to the metabolism of monoamine transmitters such as 5-hydroxytryptamine, noradrenaline and dopamine, and with the increasing aging of the population, the incidence rate of mental diseases for senior people will become increasingly higher, and senile dementia, depressive disorder and/or anxiety disorder are the most prominent ones among them.

Such diseases, which have a high incidence rate and which are difficult to eradicate, have created a huge market for 5-hydroxytryptamine and/or noradrenaline and/or dopamine (re) uptake inhibitors.

The application of *Piper laetispicum* C.DC. is rarely recorded, and only "Flora of China" and "Chinese Herbal Medicines" (2000 edition) have carried limited descriptions from the perspective of botany. The record in "Chinese Herbal Medicines" is: "The drug material is warm in nature, has acrid flavor, is used to promote blood flow, alleviate swelling and stop pain, is indicated for the treatment of injury, blood clot, swelling and pain, and should be decocted for oral administration or infused in wine . . . ."

Through years of research work and experiments, the inventor has found out that its extracts have outstanding anti-depression activity, and some biological activities for resisting anxiety, relieving pain and calming.

Before this, the inventor was already involved in two applications for China invention patents, and the first patent application (application number 00119452.6) disclosed the application of *Piper laetispicum* C.DC. and its extracts in preparing drug combinations; the second patent application (application number 03115911.7) disclosed a method for preparing *Piper laetispicum* C.DC. extracts by using its active components, and the extracts prepared and obtained by using this method can be used to treat and prevent depressive disorder or other affective disorders.

However, in subsequent research work, it has been discovered that the reflux method previously used in the extraction process involves complicated procedures and a longer period of time due to the need for operations such as heating, filtering and concentration, and is therefore more difficult to implement; what is more important is that the reflux method causes greater damage to the active components in the extracts, which results in poor pharmacological activity and safety of the extracts, and improvement is therefore necessary.

PURPOSE OF INVENTION

The primary purpose for this invention is to overcome the drawbacks that exist in the previous method for preparing *Piper laetispicum* C.DC. extracts, so as to provide a type of improved method for preparing *Piper laetispicum* C.DC. extracts with high efficiency, which not only avoids the damage to active components as incurred by high temperature heating during extraction, but also makes the preparation process convenient and easy to control.

The second purpose for this invention is to provide the *Piper laetispicum* C.DC. extracts prepared and obtained by making use of the method as mentioned.

The third purpose for this invention is to provide the application of the *Piper laetispicum* C.DC extracts as mentioned.

SUMMARY OF THE INVENTION

To implement the above-mentioned purposes, the method in this invention for preparing *Piper laetispicum* C.DC. extracts includes the following procedures:

The *Piper laetispicum* C.DC. drug material, including root, rhizome, rattan, leaf and fruit or entire plant, is pretreated first, is then impregnated or percolated with organic solvent at normal temperature or $\leq 70°$ C. to obtain crude extract solution, and is thereafter concentrated and dried at $\leq 70°$ C. to obtain the extract;

The crude extract solution in the above procedure can also be further refined, and is then concentrated and dried at $\leq 70°$ C. to obtain the refined extract; the refining methods include but are not limited to: macroporous adsorptive resin method, polyamide column method, silica gel column method, ion exchange method, alcohol extraction water sedimentation method and acid extraction alkali sedimentation method.

Or after *Piper laetispicum* C.DC. is pretreated, the supercritical fluid extraction method (SFE) is directly used to prepare and obtain extract.

The *Piper laetispicum* C.DC. crude extract or refined extract obtained through the above-mentioned method in this invention is semisolid in the form of sticky paste, viscid, yellowish-brown to pitchy in color, and is insoluble in water. The alkaloids contained include: N-isobutyl deca-trans-2-trans-4-diene amide, 1-[(2E,4E)-2,4-decadiene acyl]pyrrolidine, 3',4'-methylenedioxy cassic acid-isobutyl amide, 5'-methoxyl-3',4'-methylenedioxy cassic acid-isobutyl amide, piperamide C5:1(2E), 5'-methoxyl-3',4'-methylenedioxy cassic acid-pyrrolidine, 4,5-dihydro piperlonguminine, and piperamide.

The curative dose of the refined extract for mouse is $ED_{50}$: 4.56 mg/kg (FST), 3.49 mg/kg (FHT); rat $ED_{50}$: 1.85 mg/kg (FST). The safe dose of the refined extract for mouse is $LD_5/ED_{50}$=116-124 (FST).

The in vitro test and the mechanism of action test indicate that the *Piper laetispicum* C.DC. extract obtained through the method in this invention has prominent (re) uptake inhibiting effect on noradrenaline (NA) and/or 5-hydroxytryptamine (5-HT) and/or dopamine (DA), and when compared with the extract prepared by using the existing reflux method, it has the advantages of increasing the alkaloid content and the biological activity of the extract. Therefore, the *Piper laetispicum* C.DC. extract of this invention may serve as the noradrenaline and/or 5-hydroxytryptamine and/or dopamine (re) uptake inhibitor for development into antidepressant drug, anti-anxiety drug, sedative hypnotic, and anti-senile dementia drug. Therefore, it can serve as a component or part of the components in drugs, healthcare products or food additives for use to treat and/or prevent schizophrenia, mania, mood disorders, mutism, organic psychosyndrome, compulsion, depressive disorder, anxiety disorder, sleep disorder, epilepsy, Parkinson's syndrome, headache, neuralgia, senile dementia, and (mental) diseases related to metabolic imbalances of NA, 5-HT, DA, and like neurotransmitters.

SPECIFIC IMPLEMENTATION METHODS

The following is a further description of this invention in combination with specific cases of implementation. It should be understood that the following cases of implementation are only used to describe this invention and are not used to limit the scope of this invention.

Case of Implementation 1. Preparation of *Piper laetispicum* C.DC. Extract

Based on what is shown in Table 1, the root, rhizome, rattan, leaf and fruit or entire plant of *Piper laetispicum* C.DC. are respectively taken for preparing *Piper laetispicum* C.DC. extract, and the specific procedures are provided below:

Sample 1-1: 1 kg of the dry root and rhizome of *Piper laetispicum* C.DC. is taken and cut into segments, alcohol at about 90% is added for impregnating at normal temperature for about 48 hours, alcohol at the same concentration is then added to 20 L, percolation is performed to obtain crude extract, 15 L of warm water is added into the percolate for thorough mixing, the diluted percolate is then moved to D101 macroporous adsorptive resin (Tianjin Dajun Technology Development Co., Ltd., Resin Branch) column, and is eluted with 40% and 90% alcohol in sequence after flowing through, and the liquid eluted with 90% alcohol is collected, and is concentrated and dried at ≦70° C. to obtain refined extract.

Sample 1-2: 1 kg of the root and rhizome of *Piper laetispicum* C.DC. is taken and cut into segments, alcohol at about 80% is added for impregnating at normal temperature for about 48 hours, alcohol at the same concentration is then added to 10 L, slight heating to 50° C. is performed for percolation to obtain crude extract, the crude extract solution is vacuum concentrated to 2 L at 60° C., and alcohol at 40% is added to 10 L, the solution is then moved to HPD100 macroporous adsorptive resin (Hebei Bonherb Technology Co., Ltd.) column, and is eluted with 50% and 80% alcohol in sequence after flowing through, and the liquid eluted with 80% alcohol is collected, and is concentrated and dried at ≦70° C. to obtain refined extract.

Sample 2: 1 kg of the rattan and leaf of *Piper laetispicum* C.DC. is taken and powdered, alcohol at about 90% is added for impregnating at normal temperature for about 24 hours, alcohol at the same concentration is then added to 16 L, percolation is performed to obtain crude extract, the crude extract is then concentrated with reduced pressure at 60° C. to ⅓ of the total volume, equivalent amount of cold water is added and agitated, the precipitate is filtered off after refrigeration for 3 days, and refined extract is finally obtained through concentration and drying at ≦70° C.

Sample 3: 1 kg of the whole plant of *Piper laetispicum* C.DC. is taken and cut into segments, 10 L of 0.5% acetic acid solution is added for impregnating for 24 hours, percolation is performed to obtain crude extract, 2 L of 2% of ammonia water is then added for mild shaking, chloroform is added thereafter for extraction, and the extract is concentrated and dried at ≦70° C. to obtain refined extract.

Sample 4: 1 kg of the root and rhizome of *Piper laetispicum* C.DC. is taken and cut into segments, 55% alcohol is added for impregnating at normal temperature for about 24 hours, alcohol at the same concentration is then added to 20 L, slight heating to 60° C. is performed for percolation to obtain crude extract, the crude extract is moved to the silica gel column (silica gel H, Shandong Qingdao Ocean Chemical Group Company) for separation after having been concentrated and dried, and is eluted in sequence with cyclohexane-ethyl acetate and petroleum ether-acetone as mobile phase, the effluent liquid of petroleum ether-acetone at the portion from 10:1 to 2:1 is collected, and is concentrated and dried at ≦70° C. to obtain refined extract.

Sample 5: 1 kg of the root and rattan of *Piper laetispicum* C.DC. is taken and powdered, 5 L of ether is added for sealed impregnating at normal temperature for about 24 hours, the extract is then collected, and it is repeated 3 times. The extract is combined for recovery of ether, is then dissolved with acetone, is processed with polyamide (Xiangtan Zhaotan Chemical Plant), and is concentrated and dried at ≦70° C. to obtain refined extract.

Sample 6: 1 kg of the root and rhizome of *Piper laetispicum* C.DC. is taken and cut into segments, 5 L of 0.5% acetic acid water is added for cold impregnating for 24 hours, slight heating at ≦70° C. is thereafter performed with the opening uncovered, the water solution is then moved to the ion exchange column (732 cation exchange resin, Hebi Xiangyang Resin Plant) for processing, and is eluted with 2% ammonia water after having been enriched, and the eluant is concentrated and dried at ≦70° C. to obtain refined extract.

Sample 7: 1 kg of the root and rattan of *Piper laetispicum* C.DC. is taken and powdered, chloroform is added for sealed impregnating at normal temperature for about 24 hours, chloroform is then added to 10 L for percolation to obtain crude extract, and after chloroform is recovered, the product is obtained through direct concentration and drying at ≦70° C.

Sample 8: 1 kg of the whole plant of *Piper laetispicum* C.DC. is taken and powdered, proper amount of ethyl acetate is added for impregnating at normal temperature for about 24 hours, ethyl acetate is later added to 10 L for percolation to obtain crude extract, and after ethyl acetate is recovered, alcohol is added for dissolution, the alcohol solution is then moved to D860021 macroporous adsorptive resin (Shandong Lukang Pharmaceutical Group Co., Ltd.) column for refining, is eluted with 40% and 90% alcohol in sequence, and the eluant eluted with 90% alcohol is collected, and is concentrated and dried at ≦70° C. to obtain refined extract.

Sample 9: 1 kg of the root of *Piper laetispicum* C.DC. is taken and cut into segments, 2 L of 0.5% ammonia water is added for impregnating for 24 hours, ether is added for extraction for three times, and after the extract is combined and ether is recovered, it is concentrated and dried at ≦70° C. to obtain refined extract.

Sample 10 (control): 1 kg of the root and rhizome of *Piper laetispicum* C.DC. is taken and turned into crude powder, 60% alcohol is added for refluxing 2 times in water bath, the filtrate is combined after filtering, and is concentrated to 14% of the original filtrate volume, and 30% alcohol solution is added to obtain clear and nontransparent dilute solution, and the solution is then moved to the macroporous adsorptive resin column, and is eluted respectively with 40%, 55% and 80% alcohol in sequence, and the liquid eluted with 80%) alcohol is collected, and is concentrated and dried to obtain the effective part extract (operated in accordance with Case of Implementation 1 in China patent application with the application number as 03115911.7).

Sample 11: The whole plant of *Piper laetispicum* C.DC. is taken for preparing extract through supercritical fluid extraction method, and the specific procedures are provided below:

*Piper laetispicum* C.DC. drug material is taken, turned into crude powder and put into extraction tanks, the extraction separation tanks are heated to the predetermined status, and the pressure is raised to the predetermined value to start dynamic extraction, 200 g is fed each time, and the extraction conditions used are: pressure at 30 MPa, temperature at 40□, extraction time at 2 hours, and $CO_2$ flow at 20 $m^2$/h. The separation tanks are reduced to normal pressure through pressure reducing valve to obtain the extract.

1,000 prefabricated empty capsules, and the opening of the capsule is sealed to get the product, and each capsule is filled with 100 mg of the material, in which the amount of the refined extract is 10 mg.

2.2 Granule

Formula:

20 g of *Piper laetispicum* C.DC. extract; 380 g of soluble starch; 200 g of dextrin.

Preparation Method:

The extract is thoroughly mixed with the soluble starch and dextrin and is pressed into large flakes, and is then sieved in whole granules and dried, and the granules are subpackaged into 1,000 bags to get the product.

2.3 Tablet

Formula:

30 g of *Piper laetispicum* C.DC. extract; 100 g of starch; 30 g of dextrin; 20 g of sugar; 12 g of talcum powder; 5 g of magnesium stearate; 3 g of antioxidant.

Preparation Method:

Starch, dextrin and sugar are added before the extract is dried for making into granules, and talcum powder, magnesium stearate and antioxidant are added after the granules are dried, the granules are evenly compressed into 1,000 tablets, which are coated to get the product.

TABLE 1

Preparation of *Piper Laetispicum* C.DC. Extract

| Sample No. | Drug Materials | Pretreatment | Organic Solvent | Extracting Method | Refining Method |
|---|---|---|---|---|---|
| 1-1 | Root and rhizome | Cut | Alcohol | Percolation | Macroporous resin |
| 1-2 | Root and rhizome | Cut | Alcohol | Hot percolation | Macroporous resin |
| 2 | Rattan and leaf | Powdered | Alcohol | Percolation | Alcohol extraction water sedimentation method |
| 3 | Whole plant | Cut | Acid water | Impregnation | Acid extraction alkali sedimentation method |
| 4 | Root and rhizome | Cut | Alcohol | Hot percolation | Silica gel column |
| 5 | Root and rattan | Powdered | Ether | Impregnation | Polyamide column |
| 6 | Root and rhizome | Cut | Acid water | Percolation | Ion exchange |
| 7 | Root and rattan | Powdered | Chloroform | Percolation | — |
| 8 | Whole plant | Powdered | Ethyl acetate | Percolation | Macroporous resin |
| 9 | Root | Cut | Water containing soda | Impregnation | Organic solvent extraction |
| 10* | Root and rhizome | Powdered | Alcohol | Reflux | Macroporous resin |
| 11 | Whole plant | Powdered | | Supercritical fluid extraction | |

\**Piper laetispicum* C.DC. extract prepared through reflux method as control

Case of Implementation 2. Use of *Piper laetispicum* C.DC. Extract for Preparation of Drugs The *Piper laetispicum* C.DC. extract obtained in Case of Implementation 1 is used as drug material, and can be prepared in various dosage forms according to the conventional production method in the pharmaceutical field, such as capsules, tablets, granules, powder, drop pills, micro pills, injections, injectable powders, orally administered liquid preparations, delayed release and controlled release preparations and targeting preparations. Because the production methods for various dosage forms are the conventional methods in existing technology, capsules, granules and tablets are prepared in this case of implementation only by using the *Piper laetispicum* C.DC. extract sample 1-1 obtained in the previous case of implementation as an example.

2.1 Capsule

Formula:

10 g of *Piper laetispicum* C.DC. extract; 80 g of cornstarch; 8 g of magnesium stearate; 2 g of antioxidant.

Preparation Method:

The extract is thoroughly mixed with the starch, magnesium stearate and antioxidant, sieved, and evenly filled into Case of Implementation 3. Effect of In Vitro Inhibition on the Reuptake of 5-Hydroxytryptamine, Noradrenaline and Dopamine Research indicates that the most important physiological mechanism for noradrenaline elimination and inactivation in synaptic cleft is the reuptake at the nerve terminal, and cocaine, some phenethylamine chemical compounds and antidepressant drugs can all inhibit its process of reuptake, which is one of the most important mechanisms for antidepressant drugs to result in downward adjustment of adrenaline receptors. The physiological mechanism for the serotoninergic and dopaminergic functions is similar to that for 5-hydroxytryptamine. Clinically, there are many antidepressant drugs that can block the reuptake of noradrenaline and/or 5-hydroxytryptamine and/or dopamine. This experiment can be used to test whether or not a chemical compound inhibits the reuptake function of rat brain synaptosome and to test its potential value for use as a monoamine transmitter (re) uptake inhibitor such as an antidepressant drug.

First of all, the method of Whittaker et al (Whittaker V P & Barker L A. The subcellular tractionation of brain tissue with special reference to the preparation of synaptosomes and their component organelles. In: Fried R. ed. In Methods in Neurochemistry, Vol. New York: Marcel Dakker, Inc, 1972) is referred to for preparing brain synaptosome, and the specific procedures are: decapitate the rat and take out the cerebrum quickly, place it in precooled normal saline, and remove cerebral pia mater and vascular tissues. Take cerebral cortex, and place it in cold sugar solution. Use ultrasonic cell disruptor for producing homogenate and centrifuging to obtain refined brain synaptosome for future use.

With reference to "Modern Medical Experimental Methods" (Wang Qian as chief editor, Beijing People's Medical Publishing House, 1997) and "Modern Methodology in Pharmacological Experiment" (Zhang Juntian as chief editor, joint publication by Beijing Medical University and Peking Union Medical College, 1998), Tris-Krebs buffer is first added into the test tubes, synaptic knob suspension is added after that, and 10 µl of *Piper laetispicum* C.DC. extract (Sample 1-1) is then added, which is thoroughly mixed, and the tubes are placed in 37° C. water bath for a warm bath. 10 µl of substrate ($^3$H-5HT, $^3$H-NA or $^3$H-DA; final reaction concentration: 300 nM) is added in a 4° C. environment and is thoroughly mixed, and the tubes are placed in a 37° C. water bath for a warm bath for 5 minutes. After that, precooled Tris-Krebs buffer is added into each tube to terminate reaction, and the multichannel cell harvestor is immediately used for sucking filtration through fiberglass filter membrane, and the same solution in the same volume is used to wash tubes and filter. The filter membrane is removed and oven dried. The filter membrane is placed in the scintillation vial, methylbenzene scintillation fluid is added, and counting is performed with the β-liquid scintillation counter. The result is as shown in Table 3.

bition of NA is even more powerful, and only 1.6 µg/ml almost entirely inhibits brain synaptosome in NA uptake, and its action strength is equivalent to 0.1 mM of desipramine. In the same way, when the concentration increases approximately to more than 200 µg/ml, the non-specific diffusion of NA by synaptosome is also entirely inhibited, and its $IC_{50}$ is 0.34 µg/ml (final reaction concentration). The inhibition of DA by test Drug A is between 5-HT and NA, and its $IC_{50}$ is 1.1 µg/ml (final reaction concentration).

Therefore, the *Piper laetispicum* C.DC. extract of this invention is prominent in inhibition of rat brain synaptosome in (re) uptake of 5-HT, NA and DA, and can be used for preparing drugs, healthcare products or food additives to treat and/or prevent (mental) diseases related to the metabolism of monoamine transmitters such as 5-hydroxytryptamine, noradrenaline and dopamine.

Case of Implementation 4. 5-hydroxytryptophane-Induced Mouse Head Shaking 5-hydroxytryptophane (5-HTP) is a precursor substance for 5-HT, and monoamine oxidase inhibitor Pargyline can inhibit its metabolism, and the mouse's characteristic symptom—head shaking—can be observed with further administration of antidepressant drug.

The mice are randomized into groups, and intragastric administration is performed for each of the groups based on the corresponding doses as shown in Table 4, and test Drug A is the *Piper laetispicum* C.DC. extract sample 1-1 obtained in the case of implementation, and is administered once a day consecutively for 7 days, and normal saline is used as control at the same time. One (1) hour after the last administration, hypodermic injection of hydrochloric acid paxil is performed on all 4 groups of mice, and 90 minutes later, vena caudalis injection of 5-HTP is performed on all 4 groups of mice, and

TABLE 3

Inhibition of Brain Synaptosome Uptake of 5-hydroxytryptamine, Noradrenaline and Dopamine by *Piper laetispicum* C. DC. Extract

| Sample 1-1 (Final Reaction Concentration) | Positive Control Drug | Inhibition of Monoamine Uptake (CPM) | | |
|---|---|---|---|---|
| | | 5-hydroxytryptamine | Noradrenaline | Dopamine |
| | 0° C. | 1114 | 1519 | 1265 |
| | 37° C. | 1362 | 1671 | 1606 |
| | Fluoxetine (0.1 mM) | 1101 | | |
| | Desipramine (0.1 mM) | | 1499 | |
| | Paxil (1 mM) | | | 1197 |
| 0.064 µg/ml | | 1341 | 1674 | 1587 |
| 0.32 µg/ml | | 1329 | 1580 | 1326 |
| 1.6 µg/ml | | 1261 | 1490 | 1201 |
| 8 µg/ml | | 1191 | 1159 | 1003 |
| 40 µg/ml | | 927 | 1144 | 956 |
| 200 µg/ml | | 692 | 975 | 735 |
| 1,000 µg/ml | | 465 | 680 | 487 |

As can be seen from the result in Table 3, in comparison with the reuptake magnitude (CPM value) for the three monoamines at normal body temperature (37° C.) (under these conditions, the uptake of each monoamine is normal active uptake), the *Piper laetispicum* C.DC. extract of this invention at the concentration of only more than 0.064 µg/ml presents inhibition of the active uptake of the three monoamines (CPM value is lower than normal value), and when it reaches the concentration of 40 µg/ml, it entirely inhibits brain synaptosome in 5-HT uptake, and its action strength is equivalent to 0.1 mM of fluoxetine. When concentration increases to about 200~1,000 µg/ml, CPM value is lower than the CPM value at 0° C., which shows that the non-specific diffusion of 5-HT by synaptosome is also inhibited, and its $IC_{50}$ is 4.2 µg/ml (final reaction concentration). And its inhithe reactions of animals after the administration are observed and recorded, and the results are as shown in Table 4.

TABLE 4

Test Result on the Increase of 5-hydroxytryptamine P Effect Through Mouse Intragastric Administration (n = 10, Ridit inspection)

| Drug | Dose (mg/kg/d) | Degree of Head Shaking Reaction | | | | |
|---|---|---|---|---|---|---|
| | | 0 | I | II | III | VI |
| CK- | — | 6 | 4 | 0 | 0 | 0 |
| A | 20 | 0 | 3 | 1 | 2 | 4 |

TABLE 4-continued

Test Result on the Increase of 5-hydroxytryptamine P Effect Through
Mouse Intragastric Administration (n = 10, Ridit inspection)

| Drug | Dose (mg/kg/d) | Degree of Head Shaking Reaction | | | | |
|---|---|---|---|---|---|---|
| | | 0 | I | II | III | VI |
| A | 10 | 0 | 3 | 3 | 2 | 2 |
| A | 5 | 2 | 5 | 3 | 0 | 0 |

CK−: normal saline solution
Normal control in comparison with A high dose: R = 2.05 P < 0.05
Normal control in comparison with A high dose: R = 2.05 P < 0.05
Normal control in comparison with A high dose: R = 1.06
Judgment standard: U > 1.96, P < 0.05; U > 2.58, P < 0.01

As indicated by the result in Table 4, 15 minutes after 5-HTP is administered, mice start to present head shaking reactions in different degrees, and the 20 mg/kg dose group presents the most obvious head shaking symptom and has the greatest number of animals in positive reaction, while the head shaking symptom is mildest in the blank control group. The mice in the blank control group have all recovered to normal condition 2 hours later, while those in the three dose groups using test Drug A still have different degrees of head shaking symptoms. It can be seen that the *Piper laetispicum* C.DC. extract of this invention can enhance the 5-HTP induced mouse head shaking action and its inhibition of 5-HT uptake is thus verified in vivo.

Case of Implementation 5. Mouse Yohimbine Enhancement Model

Because yohimbine is an $\alpha_2$ receptor antagonist and can combine with an $\alpha_2$ receptor, it thus blocks the combination of NA with the receptor. For an antidepressant drug that inhibits NA reuptake or inhibits NA inactivation, if it is used with yohimbine, it may result in poisoning the animal to death due to an increase in NA concentration. Therefore, the purpose for this experiment is to verify through in vivo experiment the inhibition of NA reuptake by the *Piper laetispicum* C.DC. extract of this invention.

The mice are randomized into groups, and intragastric administration is performed for each of the groups based on the corresponding doses as shown in Table 5, and test Drug A is the *Piper laetispicum* C.DC. extract sample 1-1 obtained in the case of implementation, and is administered once a day consecutively for 7 days, and normal saline is used as control at the same time. One (1) hour after the last administration, hypodermic injection of yohimbine hydrochloride is performed on all 4 groups of mice, and the death rate for each of the groups is observed and recorded at 1, 2, 4, 5 and 24 hours after yohimbine is administered, and the results are as shown in Table 5.

TABLE 5

Test Results on the Enhancement of Yohimbine Toxicity Through Mouse
Intragastric Administration (n = 10)

| Drug | Dose (mg/kg/d) | Death of Animal | | | | |
|---|---|---|---|---|---|---|
| | | 1 h | 2 h | 4 h | 5 h | 24 h |
| CK− | — | 0 | 0 | 0 | 0 | 0 |
| A | 20 | 2 | 0 | 0 | 0 | 0 |
| A | 10 | 1 | 0 | 0 | 0 | 0 |
| A | 5 | 0 | 0 | 0 | 0 | 0 |
| A | 2.5 | 0 | 0 | 0 | 0 | 0 |

CK−: physiological saline solution

Animals in each of the groups all present an increase of excitability in central nervous system in different degrees 20 minutes after yohimbine is administered, which is shown in symptoms such as irritability and muscle trembling, and a few mice are bleeding from the mouth and the nose, and the animals in ADP group with dose at 20 mg/kg have the strongest reactions. As indicated by the result in Table 5, 1 hour later, death occurs in the 20 mg/kg and 10 mg/kg dose groups for test Drug A. This indicates that the *Piper laetispicum* C.DC. extract of this invention can enhance the toxic effect of yohimbine and the inhibition of NA uptake by the *Piper laetispicum* C.DC. extract of this invention is thus verified in vivo.

Case of Implementation 6. Inhibition of Monoamine Oxidase in the Brains of Mice

The biological function of monoamine oxidase (MAO) lies in its adjustment of the level for in vivo endogenous amines (noradrenaline, dopamine and 5-hydroxytryptamine) and exogenous amine substances. Based on its substrate and its inhibitor specificity, monoamine oxidase can be divided into two types (MAO-A and MAO-B). Dopamine and tyramine are two MAO substrates, 5-HT and noradrenaline are Type A substrates, while β-phenethylamine and benzylamine are Type B substrates, and iprazid and tranylcypromine are non-selective inhibitors for MAO. Clorgyline is a selective inhibitor for MAO-A, and deprenyl and Pargyline are selective inhibitors for MAO-B. Because MAO inhibitors have antidepressant effects, it is therefore necessary to study whether or not the extract inhibits MAO, so as to understand more of its mechanism for antidepressant effects.

The mice are randomized into groups, and based on Table 6, intragastric administration of the corresponding doses of test Drug A (Sample 1-1 in Case of Implementation 1) is performed for each of the groups, which are administered once a day consecutively for 14 days, and normal saline is used as a control at the same time, and the positive control is paxil. One (1) hour after the last administration, the animals are put to death through neck dislocation, and the brain is immediately taken for testing MAO activity. Based on the method of Zheng Li et al (Effect of Common St. John's Wort and Extract on Monoamine Oxidase and Monoamine Transmitter, Journal of China Pharmaceutical University, 2002, 33(2): 138-141), the ultraviolet spectrophotometer is used to measure optical density value, and the results are as shown in Table 6.

TABLE 6

Inhibition of MAO-A and B in Mouse Brain by Test Drug
A in Different Concentrations (n = 10 x ± SD)

| Drug | Dose | MAO-A (OD) | MAO-B (OD) |
|---|---|---|---|
| CK− | — | 0.025 ± 0.007 | 0.04 ± 0.007 |
| CK+ | 25 mg/kg | 0.012 ± 0.005** | 0.025 ± 0.008** |
| A | 20 mg/kg | 0.024 ± 0.008 | 0.041 ± 0.008 |
| A | 10 mg/kg | 0.026 ± 0.009 | 0.039 ± 0.008 |
| A | 5 mg/kg | 0.026 ± 0.007 | 0.041 ± 0.006 |

CK−: physiological saline solution; CK+: paxil
**P < 0.01; in comparison with blank control As indicated by the results in Table 6, none of the 3 dose groups for test Drug A inhibits the MAO-A and B activity in the mouse brain. This indicates that the antidepressant effects of the *Piper laetispicum* C.DC. extract of this invention are not related to the MAO-A and B activity.

Case of Implementation 7. Mouse Swimming Test

The despair test as put forth by Porsolt et al can serve as the evaluation model for the effects of antidepressant drugs. In this model, a mouse or a rat is placed in a limited and inescapable space for swimming, and the animal can be induced to have motionless status. Such status is a reflection of the animal's despair, and the status can be inhibited by some effective antidepressant drugs.

As shown in Table 7, the mice are randomized into groups, and each of the groups respectively receives intragastric administration of the corresponding dose of Drug A (Sample 1-1 in Case of Implementation 1), B (Sample 10 in Case of Implementation 1), C (Sample 7 in Case of Implementation 1), D (Sample 3 in Case of Implementation 1), E (Sample 5 in Case of Implementation 1), F (Sample 9 in Case of Implementation 1) and G (Sample 11 in Case of Implementation 1), which is administered once a day consecutively for 14 days, and normal saline is used as control at the same time, and positive control is fluoxetine. One (1) hour after the drug is administered on Day 14, the animal is placed into a 10×20 cm glass cylinder with water depth at 8~10 cm and water temperature at 22~24° C. Beginning from the 2nd minute, the accumulated time of motionless status within 4 minutes is recorded, and the results are as shown in Table 7.

TABLE 7

| Mouse Intragastric Administration Swimming Test Result (n = 10, x ± s) | | |
|---|---|---|
| Drug | Dose (mg/kg/d) | Accumulated Motionless Time (s) |
| CK− | — | 121.4 ± 17.7 |
| CK+ | 30 | 73.7 ± 17.2** |
| A | 10 | 84.0 ± 15.3** |
| A | 5 | 93.5 ± 13.3** |
| A | 2.5 | 107.1 ± 24.8 |
| B | 10 | 112.7 ± 13.0 |
| B | 30 | 107.7 ± 12.5 |
| B | 60 | 96.6 ± 16.7* |
| C | 30 | 79.3 ± 16.5** |
| D | 30 | 68.4 ± 12.6** |
| E | 30 | 81.8 ± 8.3** |
| F | 30 | 76.7 ± 13.3** |
| G | 30 | 73.9 ± 18.2** |

CK−: normal saline solution; CK+: fluoxetine
**P < 0.01;
*P < 0.05; in comparison with blank control group
$ED_{50}$ value (A): 4.56 mg/kg As shown in the result, the motionless time for mouse in swimming is prominently reduced in the three dose groups of 20, 10 and 5 mg/kg of fluoxetine and test Drug A, and in comparison with the blank control group, P value is less than 0.01, and good antidepressant effect is already seen in the dose of 5 mg/kg, and the drug effectiveness shows a good dose-effect relationship. The activity for test Drugs C-G is equivalent in the dose of 30 mg/kg to test Drug A, and is at the same time obviously better than test Drug B in the same dose.

It can be seen that the *Piper laetispicum* C.DC. extracts (test Drugs A and C-G) of this invention have more prominent antidepressant effects, and the activity of the percolated and refined extracts is obviously higher than that for the existing *Piper laetispicum* C.DC. extract prepared and obtained through reflux technology (test Drug B).

Case of Implementation 8. Rat Swimming Test

After having fasted for 4 hours, the rats are placed in a 40×18 cm glass cylinder with water depth at 15 cm (water temperature at 25° C.) for swimming for 15 minutes, and are dried with a hot blower. Then, based on Table 8, the rats are randomized into 6 groups, and each of the groups receives intragastric administration of the corresponding dose of Drug A (Sample 1-1 in Case of Implementation 1) and B (Sample 10 in Case of Implementation 1), which is administered once a day consecutively for 14 days, and normal saline is used as control at the same time, and positive control is Venlafaxine. One (1) hour after the drug is administered for the last time, the rat swimming test begins, the swimming time is 5 minutes, and the motionless time during the 5 minutes for which they are swimming is recorded, and the results are as shown in Table 8.

TABLE 8

| Rat Intragastric Administration Swimming Test Result (n = 10, x ± s) | | |
|---|---|---|
| Drug | Dose (mg/kg/d) | Accumulated Motionless Time (s) |
| CK− | — | 243.8 ± 20.1 |
| CK+ | 30 | 211.2 ± 24.7* |
| A | 10 | 187.1 ± 38.2** |
| A | 5 | 197.4 ± 47.9* |
| A | 2.5 | 222.7 ± 20.2* |
| B | 20 | 238.6 ± 22.4 |

CK−: normal saline solution; CK+: Venlafaxine
**P < 0.01;
*P < 0.05; in comparison with blank control group
$ED_{50}$ value: 1.85 mg/kg As shown in the results, the motionless time for rats during swimming is prominently reduced in the three dose groups of 10, 5 and 2.5 mg/kg of Venlafaxine and test Drug A, and in comparison with the blank control group, P value is less than 0.05, and good antidepressant effect is already seen in the dose of 2.5 mg/kg, and the drug effectiveness shows a good dose-effect relationship.

Through comparison, it is discovered that the biological activity for the *Piper laetispicum* C.DC. extract (test Drugs A) of this invention in the dose of 2.5 mg/kg is higher than that for test Drug B (prepared through reflux method) in the dose of 20 mg/kg, which indicates that the biological activity for the *Piper laetispicum* C.DC. extract of this invention obtained through the percolating and refining preparation technology is obviously higher than that for the existing *Piper laetispicum* C.DC. extract (test Drug B) prepared and obtained through reflux technology.

Case of Implementation 9. Mouse Tail Suspension Test

The tail suspension test is a simple and easy experimental method introduced by Stern et al in 1985 for evaluation of antidepressant drugs. Under inescapable stress conditions, the motionless status as displayed by rodents is a reflection of despair, which can be a simulation of human depressive status. Clinically effective antidepressant drugs can reduce the motionless time of the mouse after it cannot successfully escape through its efforts following being suspended at the tail.

The mice are randomized into groups, and each of the groups receives intragastric administration of the corresponding dose of Drag A (Sample 1-1 in Case of Implementation 1), B (Sample 10 in Case of Implementation 1), C (Sample 7 in Case of Implementation 1), D (Sample 3 in Case of Implementation 1) and E (Sample 5 in Case of Implementation 1), which is administered once a day consecutively for 14 days, and normal saline is used as control at the same time, and positive control is Venlafaxine. One (1) hour after the drug is administered for the last time, the mouse tail suspension test is performed, the duration is 6 minutes, and the stationary and motionless time within the 6 minutes is recorded, and the results are as shown in Table 9.

TABLE 9

Mouse Intragastric Administration Tail Suspension Test Result (n = 10, x ± s)

| Drug | Dose (mg/kg/d) | Accumulated Motionless Time (s) |
|---|---|---|
| CK− | — | 156.4 ± 78.6 |
| CK+ | 50 | 57.5 ± 43.0** |
| A | 20 | 80.1 ± 41.1* |
| A | 10 | 86.1 ± 43.6* |
| A | 5 | 87.5 ± 59.6* |
| A | 2.5 | 106.7 ± 40.6 |
| B | 20 | 148.6 ± 33.9 |
| C | 20 | 93.3 ± 12.4* |
| D | 20 | 89.4 ± 16.3* |
| E | 20 | 92.4 ± 12.5* |

CK−: normal saline solution; CK+: Venlafaxine
**P < 0.01;
*P < 0.05; in comparison with blank control group
$ED_{50}$ value: 3.49 mg/kg As shown in the result, the motionless time for mouse is prominently reduced in the three dose groups of 20, 10 and 5 mg/kg of Venlafaxine and test Drug A, and in comparison with the blank control group, P value is less than 0.05, the difference of drug strength among the three dose groups is not obvious, good antidepressant effect is already seen in the dose of 5 mg/kg, and the drug effectiveness shows a good dose-effect relationship. The drug strength for test Drug A in the three dose groups is slightly weaker than that for Venlafaxine in the dose of 50 mg/kg, but there is no significant difference from the perspective of statistics. The activity for test Drugs C-E is equivalent to the dose of 20 mg/kg for test Drug A, and is at the same time obviously better than test Drug B in the same dose.

Through comparison, it is discovered that the biological activity for the extract (for example, test Drugs A) of this invention in the dose of 2.5 mg/kg is already higher than that for test Drug B in the dose of 20 mg/kg, which indicates that the biological activity for the extract of this invention obtained through the percolating and refining preparation technology is obviously higher than the activity for the extract (test Drug B) obtained through the reflux technology as involved in the previous patent 03115911.7.

Case of Implementation 10. Anti-anxiety Effect—Mouse Four Board Test

The mice are randomized into groups, and are respectively given test drugs based on Table 10, namely Drug A (Sample 1-1 in Case of Implementation 1), B (Sample 10 in Case of Implementation 1), C (Sample 7 in Case of Implementation 1), F (Sample 9 in Case of Implementation 1) and G (Sample 11 in Case of Implementation 1), and normal saline is used as control, and positive control group is diazepam. The mouse is placed on the boards 30 minutes after the drug is administered, and is made to explore for 15 seconds. After that, whenever the mouse moves from one board to another board, one electric shock is given with amperage at 0.35 mA and duration time at 0.5 s. The mouse should present an obvious escape response because of this, and usually moves across 2 boards or 3 boards, if the mouse continues to run, no electric shock is given for 3 minutes thereafter. The number of electric shocks within 10 minutes is recorded, and the results are as shown in Table 10.

TABLE 10

Anti-anxiety Effect Test Result (n = 8, x ± s)

| Drug | Dose (mg/kg/d) | Accumulated Number of Electric Shocks |
|---|---|---|
| CK− | — | 4.80 ± 1.63 |
| CK+ | 1 | 12.78 ± 2.05** |
| A | 20 | 8.64 ± 2.14* |
| A | 10 | 7.43 ± 1.32* |
| B | 20 | 5.08 ± 1.05 |
| B | 40 | 7.32 ± 1.01* |
| C | 20 | 7.65 ± 2.09* |
| F | 20 | 8.98 ± 3.21* |
| G | 20 | 9.67 ± 1.72* |

CK−: normal saline solution; CK+: diazepam
**P < 0.01;
*P < 0.05; in comparison with blank control group As indicated by the result in Table 10, electric shock can significantly reduce the locomotive activity of mouse, while diazepam and the *Piper laetispicum* C.DC. extracts (test Drugs A, C, F and G) of this invention can increase the number of electric shocks, which indicates that the *Piper laetispicum* C.DC. extracts of this invention have relatively strong anti-anxiety effects, and its biological activity in the same dose is higher than that for the existing *Piper laetispicum* C.DC. extract (test Drug B) prepared and obtained through reflux technology.

Case of Implementation 11. Sedation—Open Field Test

The mice are randomized into groups, and are respectively given test drugs based on Table 11, namely Drug A (Sample 1-1 in Case of Implementation 1), C (Sample 7 in Case of Implementation 1) and B (Sample 10 in Case of Implementation 1), and normal saline is used as control at the same time, and positive control group is kavalactone extract. The mouse is placed into a cylindrical box 35 cm in height 30 minutes later, and the bottom of the box is equally divided into square grids with side length at 5 cm. After the mouse gets adapted to the environment for 3 minutes, the number of grids that the mouse has climbed within 5 minutes thereafter is recorded beginning from the $4^{th}$ minute, and the results are as shown in Table 11.

TABLE 11

Sedation Test Result (n = 8, x ± s)

| Drug | Dose (mg/kg/d) | Accumulated Number of Grids Climbed |
|---|---|---|
| CK− | — | 167.38 ± 8.70 |
| CK+ | 100 | 136.43 ± 6.86* |
| A | 40 | 133.87 ± 9.41* |
| A | 20 | 154.74 ± 10.23 |
| C | 40 | 139.78 ± 9.61 |
| B | 40 | 151.33 ± 5.72 |

CK−: normal saline solution; CK+: kavalactone extract
**P < 0.01;
*P < 0.05; in comparison with blank control group As indicated by the results in Table 11, kavalactone extract and the *Piper laetispicum* C.DC. extracts of this invention can both reduce the number of grids that the mouse climbs, which indicates that the *Piper laetispicum* C.DC. extracts (test Drugs A and C) of this invention have relatively strong sedative effects and that their biological activity is higher than that for the existing extract (test Drug B) prepared and obtained through reflux technology.

Case of Implementation 12. Analgesic Effect—Writhing Test

A chemical stimulant with definite solvents and at a definite concentration is injected into the abdominal cavity of the mouse to stimulate splanchnoderm and peritoneum parietale so as to cause deep, large-area and long-time inflammatory pain and result in behavioral reactions in the mouse such as concaving the abdomen, extending the trunk and back limbs and raising the buttocks, which are called the writhing response. The response has a high frequency of occurrence within 15 minutes after injection, and therefore, the number of instances of writhing or the number of mice with such responses within 15 minutes after injection is the quantitative index for sedation.

The mice are randomized into groups, and are respectively given test drugs based on Table 12, namely Drug A (Sample 1-1 in Case of Implementation 1), C (Sample 7 in Case of Implementation 1) and B (Sample 10 in Case of Implementation 1), and normal saline is used as control at the same time, and positive control group is acetyl salicylic acid. The mice are respectively injected intraperitoneally with 0.20 ml of 0.02% benzoquinone water solution 30 minutes later, and are immediately placed into a box with four sides sealed, and, beginning from the first occurrence of writhing responses in the mice, time is kept for 10 minutes, and the number of writhing responses in the mice is recorded within 10 minutes thereafter, and the results are as shown in Table 12.

TABLE 12

Analgesic Effect Test Result (n = 10, x ± s)

| Drug | Dose (mg/kg) | Accumulated Number of Writhing Responses |
|---|---|---|
| CK− | — | 29.25 ± 2.62 |
| CK+ | 50 | 9.89 ± 1.09** |
| A | 80 | 10.34 ± 1.44** |
| A | 40 | 14.25 ± 2.47* |
| C | 80 | 16.25 ± 0.90* |
| B | 80 | 20.97 ± 1.23 |

CK−: normal saline solution; CK+: acetyl salicylic acid
**$P < 0.01$;
*$P < 0.05$; in comparison with blank control group As indicated by the result in Table 12, acetyl salicylic acid and the *Piper laetispicum* C.DC. extracts (test Drugs A and C) of this invention can both reduce the number of writhing responses in the mice, which indicates that the *Piper laetispicum* C.DC. extracts of this invention have relatively strong analgesic effect, and their biological activity is higher than that for the existing *Piper laetispicum* C.DC. extract (test Drug B) prepared and obtained through reflux technology.

With regard to the *Piper laetispicum* C.DC. extract as disclosed in the China patent applications submitted previously by the applicant with the application numbers respectively as 00119452.6 and 03115911.7, because the reflux method is used for preparation, the operation at relatively high temperature as used in the process produces greater damage to the active components in the extract, which results in poor pharmacological activity and safety for the extract. On the other hand, the method of this invention involves the use of impregnation, percolation and low-temperature concentration and drying, and therefore produces less damage to the active components in the extract, which retains to a great extent components such as alkaloid and lignans, and in comparison with the existing extract prepared and obtained through reflux method, the biological activity for the *Piper laetispicum* C.DC. extracts of this invention has been prominently increased.

It is not difficult to see from the above cases of implementation that the *Piper laetispicum* C.DC. extracts prepared and obtained through the method of this invention can effectively inhibit the reuptake of monoamine transmitters such as 5-hydroxytryptamine, noradrenaline and dopamine and can therefore be used to prepare drugs, healthcare products or food additives for treating and/or preventing mental diseases related to monoamine transmitter metabolism. The monoamine transmitter metabolism related diseases include, but are not limited to: schizophrenia, mania, mood disorders, mutism, organic psychosyndrome, compulsion, depressive disorder, anxiety disorder, sleep disorder, epilepsy, Parkinson's syndrome, headache, neuralgia and senile dementia.

What is claimed is:

1. A method of preparing an extract of *Piper laetispicum* C. DC. comprising: maserating *Piper laetispicum* C. DC., combining the maserated *Piper laetispicum* C. DC. with at least one organic solvent to form a combination, impregnating or perculating the combination at room temperature and without refluxing the combination, thereby obtaining an extract of *Piper laetispicum* C. DC. with an improved biological activity, wherein said organic solvent is selected from the group consisting of ethanol, methanol, chloroform, ethyl acetate, and diethyl ether, and wherein said improved biological activity is selected from the group consisting of anti depressant effect, anti anxiety effect, sedative effect and analgesic effect.

2. The method of claim 1, wherein the *Piper laetispicum* C. DC. is selected from the group consisting of roots, rhizome, vines, leaves, fruits and the whole *Piper laetispicum* C. DC.

3. The method of claim 1, further comprising purifying the *Piper laetispicum* C. DC extract.

4. The method of claim 3, wherein the purifying comprises the use of a macropore poly adsorbent column, a polyamide column, a silica gel column, an ion exchange column, an ethanol distill-water deposit, an acid distill-alkali deposit, or an alkali moist-organic solvent extract.

* * * * *